(12) United States Patent
Tashiro et al.

(10) Patent No.: US 8,535,231 B2
(45) Date of Patent: Sep. 17, 2013

(54) ULTRASONIC DIAGNOSTIC APPARATUS

(75) Inventors: Rika Tashiro, Ashigarakami-gun (JP); Tomohiro Nishino, Ashigarakami-gun (JP); Tsuyoshi Tanabe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 242 days.

(21) Appl. No.: 13/017,782

(22) Filed: Jan. 31, 2011

(65) Prior Publication Data

US 2011/0245670 A1    Oct. 6, 2011

(30) Foreign Application Priority Data

Mar. 30, 2010  (JP) ................................. 2010-077167

(51) Int. Cl.
*A61B 8/00*    (2006.01)
(52) U.S. Cl.
USPC ......................................... 600/443; 600/437
(58) Field of Classification Search
USPC ................................................. 600/443, 437
See application file for complete search history.

(56) References Cited

U.S. PATENT DOCUMENTS 6,416,476 B1    7/2002  Ogasawara et al.

FOREIGN PATENT DOCUMENTS

| JP | 2000-201925 A | 7/2000 |
| JP | 2008-0108015 A | 1/2008 |

*Primary Examiner* — Unsu Jung
*Assistant Examiner* — Rajeev Siripurapu
(74) *Attorney, Agent, or Firm* — Sughrue Mion, PLLC

(57) ABSTRACT

An ultrasonic diagnostic apparatus is provided with an ultrasonic probe, an ultrasonic image generating section, a head mounted display (HMD), and an orientation measurement section. The ultrasonic probe has two-dimensionally arranged ultrasonic transducers. The ultrasonic image generating section generates a 2D ultrasonic image representing a cross section of a three-dimensional area inside of a patient's body. The HMD has an orientation sensor for outputting signals corresponding to motion of the HMD and a projector for projecting images and the like within the view of an operator Op. The orientation measurement section measures rotation direction and rotation angle of the operator Op's head (HMD). A plurality of cross sections of the three-dimensional area inside of the patient's body for which the 2D image is generated is preliminary set, and the generated 2D ultrasonic image is switched according to the rotation direction and the rotation angle of the HMD.

9 Claims, 10 Drawing Sheets

OUTWARD

RETURN

OUTWARD

RETURN

ULTRASONIC DIAGNOSTIC APPARATUS

BACKGROUND OF THE INVENTION

1. Field of the Invention

The present invention relates to an ultrasonic diagnostic apparatus that transmits ultrasonic waves to the inside of a patient's body to obtain tomographic images of the patient's body, and more particularly relates to an ultrasonic diagnostic apparatus that is provided with a head mounted display.

2. Description of the Related Art

An ultrasonic diagnostic apparatus has conventionally been used widely for diagnoses and examinations in the medical field. The ultrasonic diagnostic apparatus transmits ultrasonic waves to the inside of a patient's body, and generates ultrasonic tomographic images (hereinafter, referred to as the ultrasonic images) of the patient's body from the reflected echoes, and display them on a monitor. The ultrasonic diagnostic apparatus is basically constituted of an ultrasonic probe, a processor, and the like. The ultrasonic probe, which is used with being pressed against a surface of the patient's body, transmits the ultrasonic waves to the inside of the patient's body and receives the reflected echoes from the patient's body. The processor generates the ultrasonic image based on signals output from the ultrasonic probe according to the received echoes, and displays the generated ultrasonic image on the monitor.

The ultrasonic probe is formed to such a size that an operator like doctor or examination technician (ultrasonographer) can hold with one hand, and is connected to the processor wirelessly or through a flexible communication cable. Owing to this, the ultrasonic probe can be pressed against the patient's body while freely adjusting its position and angle. Meanwhile, the monitor on which the ultrasonic image is displayed is placed at a predetermined position like bed side with the processor. As the ultrasonic probe used apart from the monitor, the operator has to change the direction of gaze often between his hands to check the position and angle of the ultrasonic probe and the monitor to check the displayed diagnostic image during the diagnosis or examination using the ultrasonic diagnostic apparatus.

In order to remove the burden of often changing the direction of gaze, a head mounted display (FIND) which displays the ultrasonic image superimposed upon the operator's view observing the hand holding the ultrasonic probe has recently been known. Moreover, there is known a HMD which displays the ultrasonic image beyond the operator's line of sight by recognizing position of the operator's pupil (Japanese Patent Laid-Open Publication No. 2008-18015).

The commonly used ultrasonic probe (hereinafter, referred to as the 2D ultrasonic probe) has ultrasonic transducers arranged in a line, and obtains reception signals to be the tomographic images of the patient's body by transmitting and receiving the ultrasonic waves in a single plane. However, a 3D ultrasonic probe has recently been known. In the 3D ultrasonic probe, the ultrasonic transducers are two-dimensionally arranged, and transmits the ultrasonic waves to a three-dimensional area inside of the patient's body and receives the ultrasonic waves therefrom, thereby obtaining three-dimensional reception signals of this area (hereinafter, referred to as the 3D data). Breast cancer, for example, is said to be cured with a 90% chance of complete recovery if it is detected at an early stage (tumor thickness: 2 cm or less), and can be cured with a 100% chance of complete recovery if it is detected at a very early stage (tumor thickness: several millimeters). However, in inserting or puncturing a biopsy needle into such a small target, it is difficult to confirm whether the biopsy needle is accurately punctured into the tumor mass by observing the common 2D tomographic image. Therefore, the 3D ultrasonic probe is used in the recent breast cancer examination, and the biopsy needle is punctured while observing the ultrasonic images in a plurality of cross sections around the tumor mass.

Furthermore, there is known an ultrasonic diagnostic apparatus provided with the 3D ultrasonic probe and the HMD. In this apparatus, when the 3D ultrasonic image three-dimensionally representing the view inside of the patient's body is displayed on the HMD after obtaining the 3D data using the 3D ultrasonic probe, the 3D ultrasonic image seen from the direction of the operator's gaze is generated and/or displayed. Owing to this, operations related to the ultrasonic diagnostic apparatus can be reduced even when both of the operator's hands are occupied for the operations of the 3D ultrasonic probe and treatment tools (U.S. Pat. No. 6,416,476 corresponding to Japanese Patent Laid-Open Publication No. 2000-201925).

When the biopsy needle is punctured using the ultrasonic diagnostic apparatus, a relatively wide view of the ultrasonic image is generally observed in advance to check the position and number of the tumor, and to determine a site to be diagnosed. The above-described 3D ultrasonic image is useful for such wide view observation. In puncturing the biopsy needle, on the other hand, the planar ultrasonic image containing the biopsy needle is more useful as compared to the 3D ultrasonic image since an insertion path of the biopsy needle needs to be determined after carefully and precisely examining tissue characterization and the like of the site to be examined and its periphery. However, the conventional ultrasonic diagnostic apparatus provided with the 3D ultrasonic probe always displays the 3D ultrasonic image. To display the planar ultrasonic image (hereinafter, referred to as the 2D ultrasonic image) in arbitrary cross section of the patient's body, setting for generating or displaying the 2D ultrasonic image in which (what types of) cross section requires complex operations, and therefore the usability of the apparatus is not necessarily good.

In this way, when the 2D ultrasonic image is generated using the 3D ultrasonic probe, there may be a method to detect the operator's line of sight first, and to generate or display the 2D ultrasonic image of the cross section vertical to the line of sight with respect to the area for which the 3D data is obtained, like the U.S. Pat. No. 6,416,476 corresponding to the Japanese Patent Laid-Open Publication No. 2000-201925. Even in the case where the 2D ultrasonic image is generated using the 3D ultrasonic probe, however, the treatment tool such as the biopsy needle can easily be lost depending on a slight change of position or tilt of the ultrasonic probe, like the case of generating the 2D ultrasonic image with the conventional 2D ultrasonic probe. Moreover, since the cross section for which the 2D ultrasonic image is generated changes in response to the change of the operator's line of sight, the operator needs to fix not only the ultrasonic probe but also the head on which the HMD is mounted so as to observe the 2D ultrasonic image in a certain cross section, which causes burden to the operator. In view of this, in generating and displaying the 2D ultrasonic image using the 3D ultrasonic probe, it is more preferable to switch the ultrasonic image in appropriate cross section with simple operation as compared to changing the cross section in response to the change in the line of sight.

SUMMARY OF THE INVENTION

An object of the present invention is to provide an ultrasonic diagnostic apparatus in which cross sections of an ultrasonic image are easily switched according to an orientation of a HMD.

In order to achieve the above and other objects, an ultrasonic diagnostic apparatus according to the present invention includes an ultrasonic probe, a tomographic image generating section, a head mounted display, a rotation measurement section, and a tomographic image switch section. In the ultrasonic probe, ultrasonic transducers for transmitting ultrasonic waves and receiving echoes of the ultrasonic waves are two-dimensionally arranged. The ultrasonic probe scans a three-dimensional area of a patient's body with the ultrasonic waves. The tomographic image generating section generates a tomographic image of the three-dimensional area of the patient's body in a cross section, based on reception signals indicative of the echoes received by the ultrasonic transducers from inside of the patient's body. The head mounted display is mounted on a head of an operator. The head mounted display includes an orientation detector and a projector. The orientation detector outputs signals corresponding to motion of the head of the operator. The projector projects at least the tomographic image in the operator's view. The rotation measurement section measures rotation direction and rotation angle of the head of the operator on which the head mounted display is mounted with reference to a predetermined orientation of the head mounted display, based on the signals output from the orientation detector. The tomographic image switch section switches the tomographic image projected by the projector. The cross section of the tomographic image is selected from a plurality of predetermined cross sections, according to the rotation direction and the rotation angle measured by the rotation measurement section.

It is preferable that at least three predetermined cross sections are defined, and the cross section is selected according to the following cases: one is where the head mounted display is in the predetermined orientation; another is where the head mounted display is horizontally rotated; and the other is where the head mounted display is vertically rotated.

In addition, it is preferable that the rotation angle for switching the tomographic image is different between an outward rotation and a return rotation. In the outward rotation, the head mounted display is rotated in a direction becoming further from the predetermined orientation. In the return rotation, the head mounted display is rotated in a direction becoming closer to the predetermined orientation.

Moreover, it is preferable that the rotation angle for switching the tomographic image is smaller in the return rotation than in the outward rotation.

It is preferable that the rotation angle for switching the tomographic image is variable.

It is preferable that a guide line indicating an insertion direction of a biopsy needle is superimposed upon the tomographic image based on at least one of the predetermined cross sections.

It is preferable that the tomographic image generating section generates the tomographic image when the ultrasonic probe and the head mounted display are both activated.

According to the present invention, the cross sections of the 2D ultrasonic image can be easily switched according to the orientation of the head mounted display. Owing to this, the insertion path of the biopsy needle can be easily conformed even if the operator's hands are occupied for the operations of the ultrasonic probe and the treatment tools when the ultrasonic diagnostic apparatus of the present invention is used in, for example, puncturing the biopsy needle. Here, the cross section for which the 2D ultrasonic image is generated is not changed in response to the change of the operator's line of sight, but selectively changed from the preliminarily set plural cross sections. Owing to this, the treatment tool like the biopsy needle is hardly lost.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
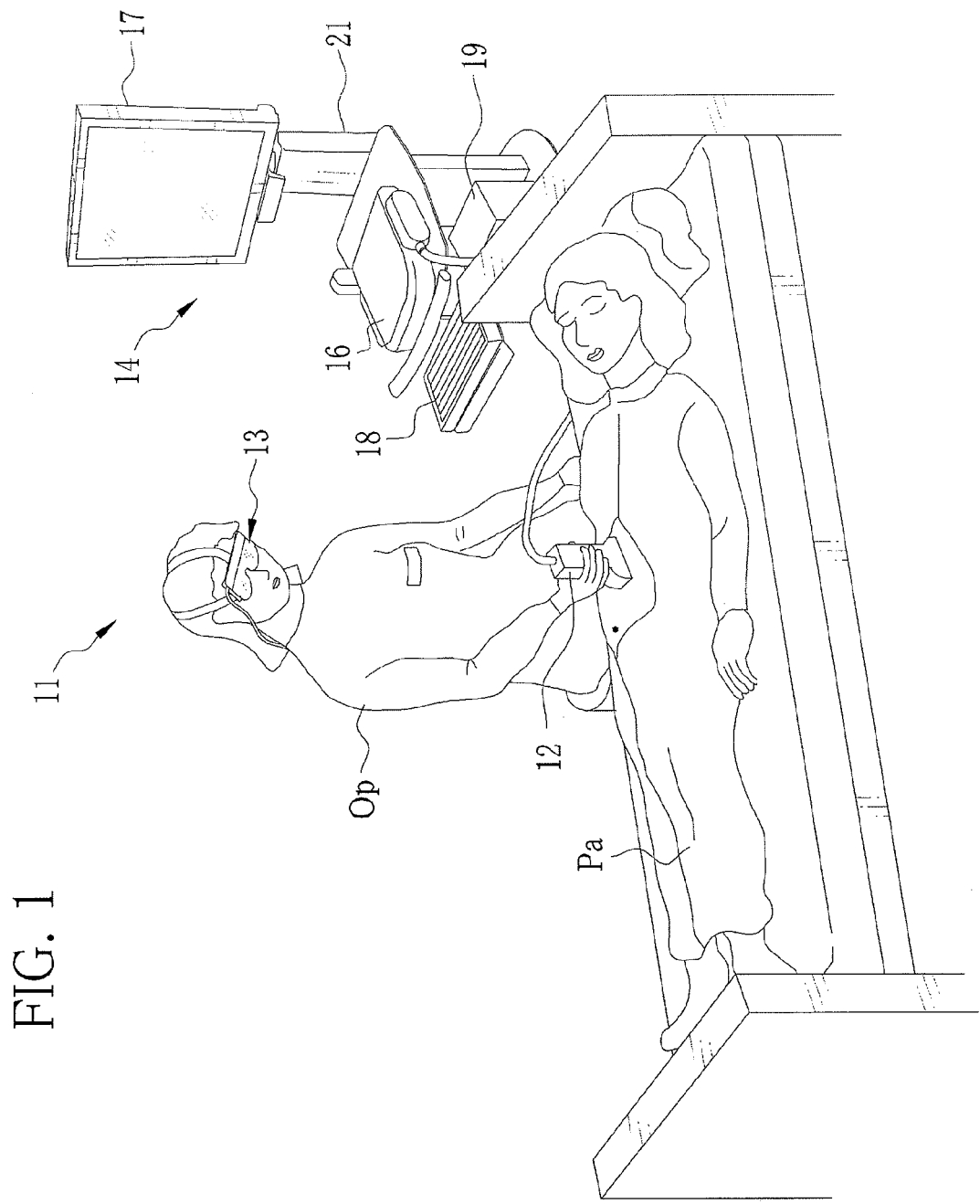
FIG. 1 is a schematic view illustrating an ultrasonic diagnostic apparatus and procedures using the ultrasonic diagnostic apparatus.

As shown in FIG. 1, an ultrasonic diagnostic apparatus 11 is an apparatus in which ultrasonic waves are transmitted to the inside of a body of a patient Pa laid quietly on a bed or the like, and an ultrasonic image which is a tomographic image of the inside of the patient's body is generated based on the echoes of the ultrasonic waves and displayed. The ultrasonic diagnostic apparatus 11 is constituted of an ultrasonic probe 12, a head mounted display (HMD) 13, and a main body 14.

The ultrasonic probe 12 for transmitting the ultrasonic waves and receiving the echoes of the ultrasonic waves is formed to such a size that an operator Op can hold with one hand. The ultrasonic probe 12 is used with being pressed against a surface of the patient Pa's body. The ultrasonic probe 12 is connected to the main body 14 through a flexible communication cable, and its position and angle to be pressed against the patient Pa can be freely adjusted within predetermined ranges. The ultrasonic probe 12 is the so called 3D ultrasonic probe, and transmits the ultrasonic waves to a three-dimensional area (hereinafter, referred to as the scanning area) inside of the patient Pa's body and also receives the echoes from the scanning area.

The HMD 13 is mounted on a head of the operator OP, and displays the ultrasonic image or the like by superposing it on the operator Op's view. The HMD 13 is the so called transmissive display which enables the operator Op to observe the patient Pa and the like directly in much the same way without mounting the HMD 13. The HMD 13 projects image light of the ultrasonic image or the like to the operator Op's eyes using an inclined surface situated in front of the operator's eyes when mounted on the operator Op. Owing to this, the operator Op recognizes a virtual image of the ultrasonic image or the like in his or her view. Moreover, the HMD 13 detects movement of the operator Op's head with a sensor incorporated therein, which is described later, and sends the information to the main body 14.

The main body 14 is constituted of a processor 16, a monitor 17, an operation section 18, a memory device 19, and the like. Each component constituting the main body 14 is placed on, for example, a movable work table 21, and located at bed side. The processor 16 controls operations of the ultrasonic probe 12 and the HMD 13, that is, the ultrasonic diagnostic apparatus 11 in response to input operation from the operation section 18 and the HMD 13. When receiving the echoes, the ultrasonic probe 12 outputs reception signals reflecting the received echoes. The processor 16 generates the ultrasonic image from the reception signals output from the ultrasonic probe 12, and makes the monitor 17 and the HMD 13 display the generated ultrasonic image. The processor 16 makes the memory device 19 store the ultrasonic image and the like in response to the input operation from the operation section 18 and the HMD 13.

Figure 2:
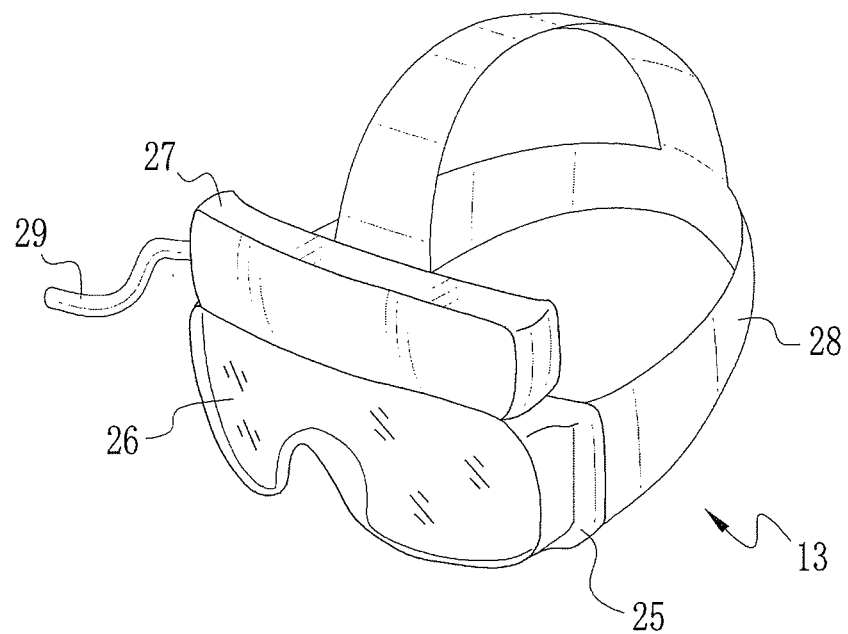
FIG. 2 is an external perspective view illustrating a head mounted display (HMD)

As shown in FIG. 2, the HMD 13 is constituted of a goggle 25 having a lens 26, a HMD control section 27, and a fixation band 28 for fixing the HMD 13 to the operator Op's head. The fixation band 28 has a band extending from side to side over the back of the head, and another band extending from top to back of the head. For this configuration, the HMD 13 is fitted to the operator Op without moving or slipping the goggle 25 and the HMD control section 27 from a predetermined mounted position when the operator Op moves his or her head.

The lens 26 is a part situated in front of the operator Op's eyes when the HMD 13 is mounted on the operator Op. Since the lens 26 is made of an almost transparent material, the view of the operator Op with HMD 13 mounted is much the same without mounting the HMD 13. An outer surface 26*a* of the lens 26 is formed almost flat to be approximately perpendicular to a line of sight of the operator Op, even though the outer surface 26*a* is curbed to fit the general shape of the head. An inner surface 26*b* of the lens 26, on the other hand, is formed to be an inclined surface inclined by a predetermined angle with respect to the line of sight of the operator Op. Moreover, the inner surface 26*b* of the lens 26 is the so called half mirror which partially transmits and reflects incident light.

The HMD control section 27 is located above and formed together with the goggle 25. When the HMD 13 is mounted on the operator Op, the HMD control section 27 is pressed against a forehead of the operator Op. The HMD control section 27 has optical systems and elements like sensors for carrying the operation of the HMD 13 incorporated therein. Owing to these optical systems and elements, the ultrasonic image or the like is displayed in the operator Op's view and the movement of the operator Op's head is detected. The HMD control section 27 is connected to the processor 16 through a flexible communication cable 29, and each element incorporated in the HMD control section 27 is operated based on control signals received from the processor 16 via the communication cable 29. In the same manner, signals output from image capturing elements and the like incorporated in the HMD control section 27 are sent to the processor 16 via the communication cable 29.

Figure 3:
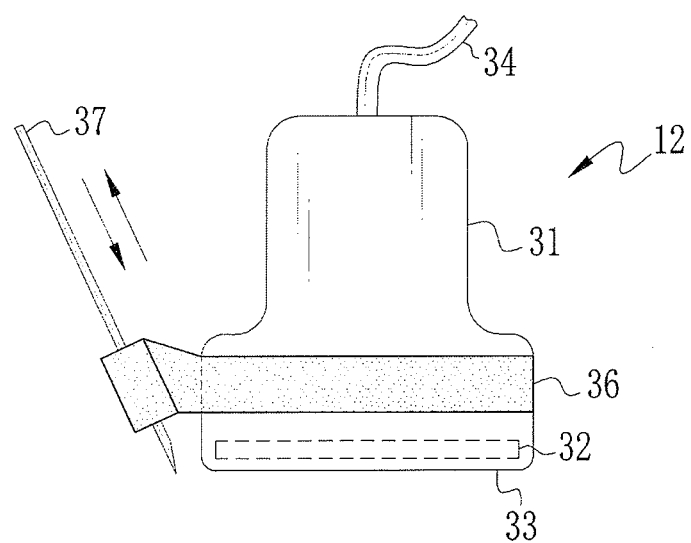
FIG. 3 is an external view illustrating an ultrasonic probe and a biopsy needle adaptor.

As shown in FIG. 3, the ultrasonic probe 12 is constituted of a holding part 31 which the operator Op holds, and a distal end portion 33 having ultrasonic transducer array 32 incorporated therein. The distal end portion 33 is pressed against the surface of the patient Pa. The ultrasonic probe 12 is connected to the processor 16 through a communication cable 34. The ultrasonic transducer array 32 is formed of ultrasonic transducers two-dimensionally arranged. The ultrasonic waves emitted from each of these ultrasonic transducers are transmitted to the scanning area inside of the patient Pa's body, and the echoes from the patient Pa's body are received with each of these ultrasonic transducers.

In addition, a biopsy needle adaptor 36 is attached to the ultrasonic probe 12. The biopsy needle adaptor 36 holds a biopsy needle 37 (treatment tool) to be freely inserted to or pulled out, and fix insertion position and insertion angle of the biopsy needle 37 against the ultrasonic probe 12. The biopsy needle adaptor 36 is attached to the distal end portion 33 when the biopsy needle 37 is punctured using the ultrasonic diagnostic apparatus 11. Note that plural types of biopsy needle adaptors 36 are prepared depending on the insertion position and angle of the biopsy needle 27 against the ultrasonic probe 12, and appropriate one is selected according to the position where the needle is punctured or the depth of the tumor or the like.

Figure 4:
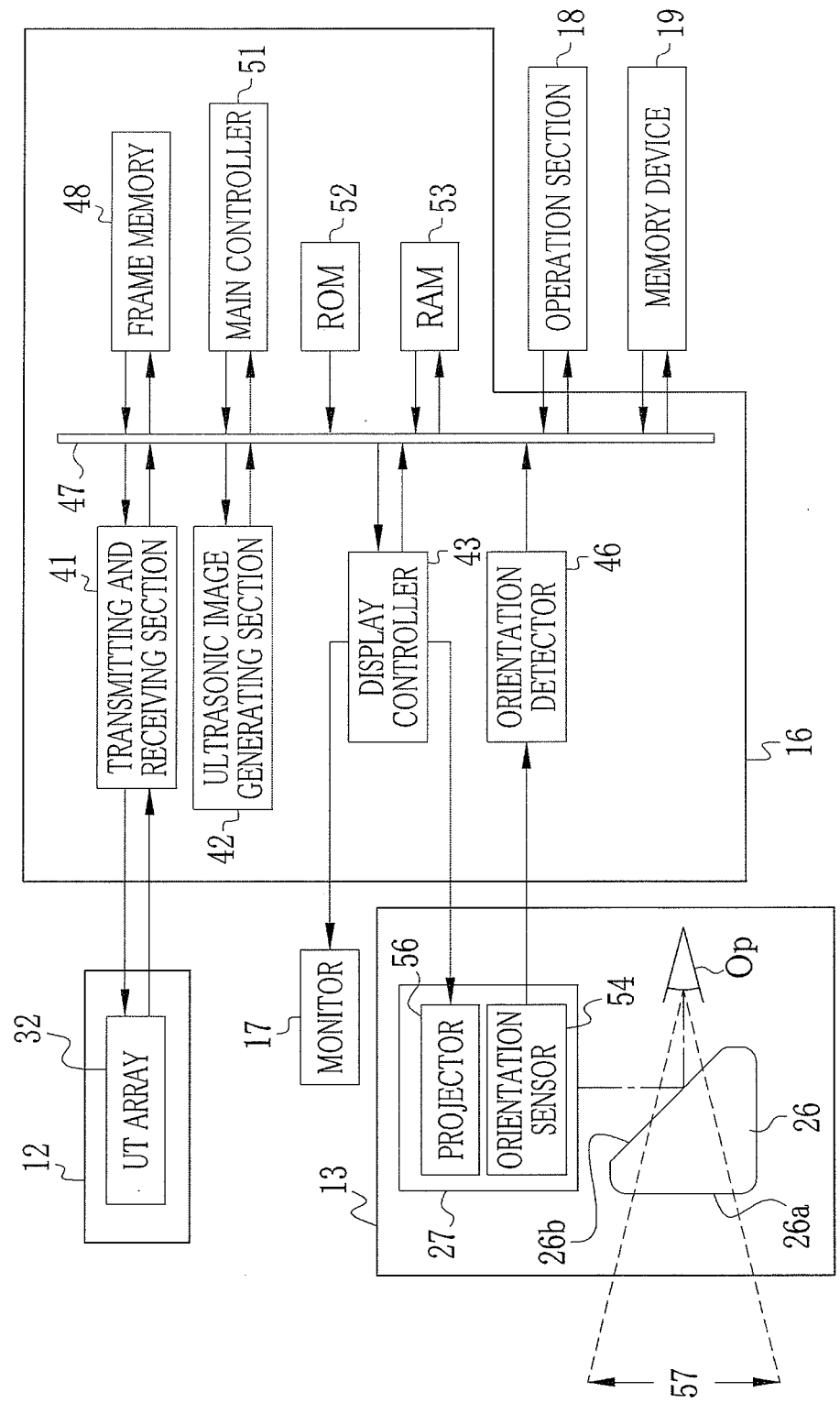
FIG. 4 is a block diagram illustrating an electrical configuration of the ultrasonic diagnostic apparatus.

As shown in FIG. 4, the processor 16 is constituted of a transmitting and receiving section 41, an ultrasonic image generating section 42, a display controller 43, and an orientation detector 46. These components are connected through a system bus 47.

The transmitting and receiving section 41 is constituted of a pulsar and a receiver. The number of the pulsars and the receivers respectively are same as the number of the ultrasonic transducers of the ultrasonic transducer array 32. The transmitting and receiving section 41 makes the ultrasonic probe 12 transmit an ultrasonic beam and receives the reception signals that are output from the ultrasonic probe 12 in response to the received echoes, using the pulsars and the receivers. For example, the transmitting and receiving section 41 selects some of the pulsars and drives them. At this time, the transmitting and receiving section 41 does not simultaneously drive all of the selected pulsars, but individually drives them at different timing. Owing to this, the ultrasonic transducer corresponding to the driven pulsar emits the ultrasonic waves, and the ultrasonic beam converged at the depth corresponding to the drive timing of the selected pulsars is transmitted. The transmitting and receiving section 41 receives the reception signals that are output from each ultrasonic transducer upon receipt of the echoes, with the corresponding receiver. The transmitting and receiving section 41 amplifies the reception signals and applies the A/D conversion to them, and thereby digitizing the reception signals. The reception signals thus digitized are input to the ultrasonic image generating section 42. The control of the transmission and reception of the ultrasonic beam by the transmitting and receiving section 41 is made by a main controller 51 described later. The main controller 51 changes the condition or type of the transmitted ultrasonic beam by changing the drive timing of the pulsar and receiver depending on the ultrasonic image or the like requested by the ultrasonic image generating section 42.

The ultrasonic image generating section 42 performs orthogonal detection processing on the reception signals input from the transmitting and receiving section 41, and each signal is converted to a complex baseband signal, thereby generating 3D data of the scanning area. In addition, the ultrasonic image generating section 42 performs reception focusing processing by phase-matching or adding on the 3D data of one frame, and generates the 3D ultrasonic image three-dimensionally describing the view inside of the patient Pa's body, or generates the 2D ultrasonic image (for example, B-mode image) in a predetermined cross section of the scanning area to and from which the ultrasonic beam is transmitted and received. The ultrasonic image generating section 42 generates the 2D ultrasonic image when the ultrasonic probe 12, which is the so called 3D ultrasonic probe, is connected to the main body 14 as well as the HMD 13 is activated and the signals are output from an orientation sensor 54, which is described later. Based on orientation signals from the orientation detector 46, the cross section of the 2D ultrasonic image to be generated is selected in the scanning area. When the HMD 13 is not connected, or when the HMD 13 is not turned on, or when the HMD 13 is not activated as the control corresponding to the motion of the operator Op's head, that is, the motion of the HMD 13 (hereinafter, referred to as the head tracking) is turned off, while the ultrasonic probe 12 is connected and activated, the ultrasonic image generating section 42 generates the 3D ultrasonic image.

The ultrasonic image generating section 42 generates the 2D ultrasonic image in a cross section selected from among a plurality of predetermined cross sections different from one another in direction with respect to the scanning area. The cross section is selected according to the movement of the head of the operator Op, which is described later. Therefore, the ultrasonic image generating section 42 has an image switch section for selecting one cross section from among the plurality of cross sections and switching the ultrasonic image to be displayed by the HMD 13 based on the selected cross section. The ultrasonic image in the specified cross section generated in the ultrasonic image generating section 42 is temporarily stored in a frame memory 48 and read out by the display controller 43. It is also possible that the 2D ultrasonic image of each cross section is preliminarily generated, and the 2D ultrasonic image corresponding to the selected cross section is readout and stored in the frame memory 48.

The display controller 43 reads out the ultrasonic image generated in the ultrasonic image generating section 42 from the frame memory 48 and displays it on the monitor 17 and the HMD 13. At this time, the display controller 43 also displays information about the patient Pa, the observed site, date and time, setting condition of the ultrasonic diagnostic apparatus 11, frequency and power of the transmitted ultrasonic waves, frame border indicating ROI, biopsy guide assisting insertion of the biopsy needle, various information such as cross section direction of the displayed 2D ultrasonic image with respect to the scanning area, setting menu, and the like on the monitor 17 and the HMD 13 along with the ultrasonic image. At this time, the display controller 43 displays such ultrasonic image and the like full screen on the monitor 17. On the other hand, the display controller 43 designates position coordinate and size of the virtual monitor screen, which is constituted of the above-described ultrasonic image and the like, in a view 57 such that the virtual monitor screen can be displayed in a partial area (hereinafter, referred to as the window) within the view 57. The position coordinate and size of the window designated by the display controller 43 is predetermined by operating the operation section 18.

The orientation detector 46 detects the movement of the operator Op on which the HMD 13 is mounted based on the signals input from the orientation sensor, which is described later, and inputs as orientation signals to the ultrasonic image generating section 42. The orientation signals output from the orientation detector 46 indicate, for example, rotation direction and rotation angle of the operator Op's head. Based on the orientation signals, the ultrasonic image generating section 42 changes the 2D ultrasonic image to be generated if the operator Op's head is rotated by the predetermined angle or more in the predetermined direction. The standard for measuring the rotation direction and the rotation angle of the operator Op's head included in the orientation signals is arbitrary set by inputting the orientation of the operator Op with the HMD 13 mounted from the operation section 18.

The main controller 51 is connected to each component of the processor 16 through the system bus 47, and takes overall control of each component. A ROM 52 stores various programs and data for controlling the operations of the ultrasonic diagnostic apparatus 11. The main controller 51 reads out the necessary programs and data from the ROM 52 and develops them in a RAM 53 to sequentially operate the read programs. The main controller 51 receives operation signals from the operation section 18, and makes each component of the ultrasonic diagnostic apparatus 11 execute operations corresponding to the input signals. Moreover, the main controller 51 detects the connection of the ultrasonic probe 12 and the HMD 13, and also notifies the connection status and operation status of such component of the ultrasonic diagnostic apparatus 11 as necessary. For example, the main controller 51 detects the connection of the ultrasonic probe 12 by the input of ID and connection of the HMD 13 by the input signals from the orientation sensor 54 later described, and the connection status and the operation status are sent to the ultrasonic image generating section 42.

In FIG. 4, the HMD control section 27 is provided with the orientation sensor 54 and a projector 56. The orientation sensor 54 detects the movement of the operator Op's head with the HMD 13 mounted, and is constituted of an angular velocity sensor like a gyro sensor. The orientation sensor 54 outputs signals (for example, angular velocity signals) corresponding to the movement of the operator Op's head with the HMD 13 mounted to the orientation detector 46.

The projector 56 is constituted of a liquid crystal display elements and projection optical systems (both not shown). The ultrasonic image and various types of information are displayed in an area corresponding to the above-described window on the liquid crystal display elements of the projector 56 by the display controller 43. The projection optical systems project the window displayed on the liquid crystal display elements to the inner surface 26*b* of the lens 26. At this time, the light from the liquid crystal display elements does not form an image but is reflected by the inner surface 26*b* of the lens 26 to enter the eyes of the operator Op. Owing to this, the operator Op recognizes the window displaying the ultrasonic image as the virtual image within the view 57.

Figure 5:
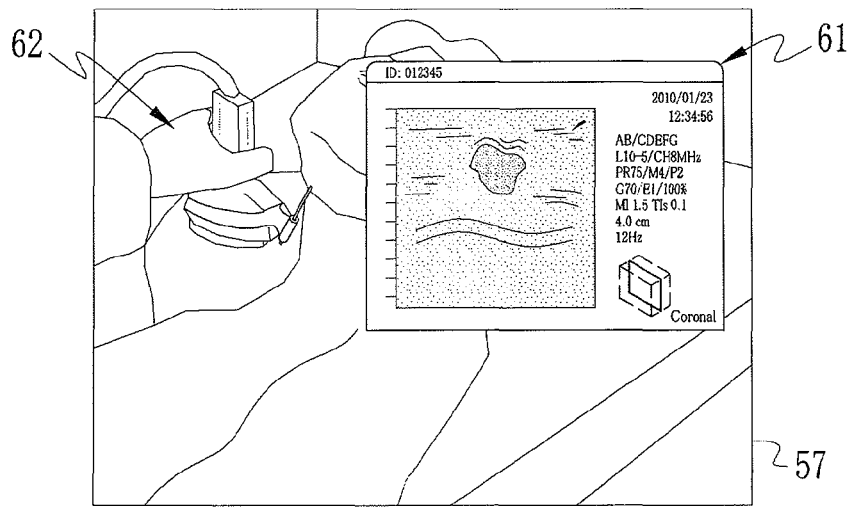
FIG. 5 an explanatory view illustrating an operator's view.

As shown in FIG. 5, the operator Op with the HMD 13 mounted can observe the view 57 through the lens 26 in almost same way without mounting the HMD 13. However, since a window 61 displaying the ultrasonic image and the like is superposed at the predetermined position in the view 57 through the HMD 13, the part showing the window 61 is absent as compared to the view without the HMD 13. At this time, the operator Op with the HMD 13 mounted may move his face to such a direction where his hands 62 holding the ultrasonic probe 12 and the like appear at the left side of the view 57 and the window 61 appears at the right side of the view 57. If the ultrasonic diagnostic apparatus 11 is used in such condition, the operator Op can observe the hands 62 and the ultrasonic image (window 61) together almost at once with little shift in the direction of gaze. The display position and the size of the window 61 are predetermined by inputting from the operation section 18.

Figure 6:
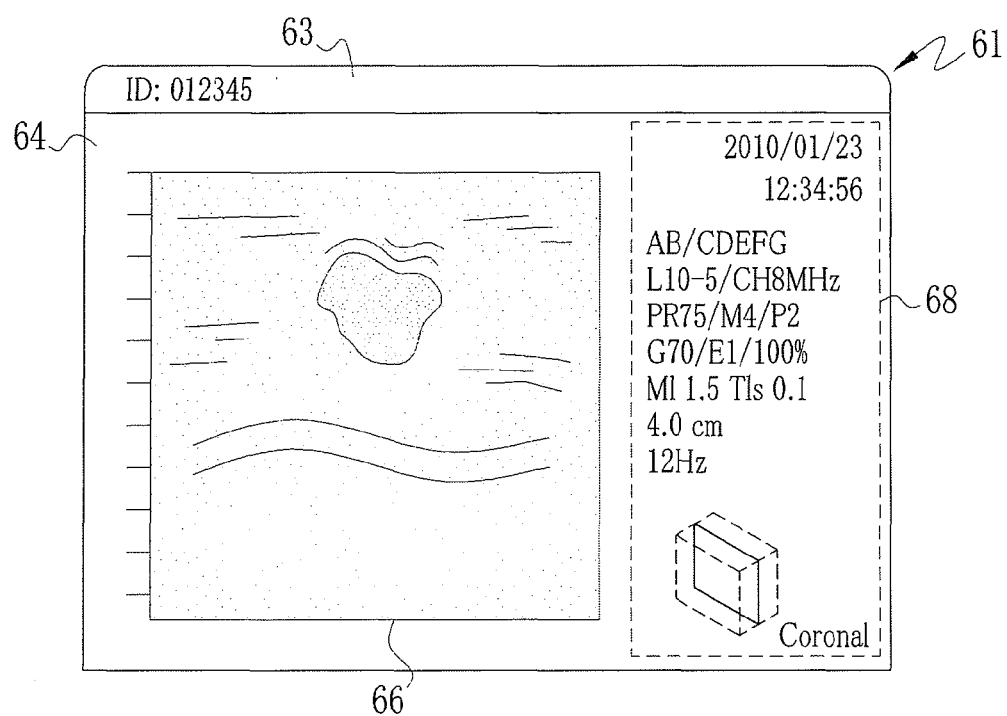
FIG. 6 is an explanatory view illustrating an example of a window displayed in the operator's view by the HMD.

As shown in FIG. 6, the window 61 displayed in the view 57 by the HMD 13 includes, for example, a title bar 63 and an image display area 64 provided below the title bar 63.

The title bar 63 displays ID of the operator Op, name of the patient Pa, the observed site, and the like. The title bar 63 is used for changing the display position of the window 61. To change the display position of the window 61 according to the line of sight input from the HMD 13, the operator Op keeps gazing at one point of the title bar 63. When the gaze is detected by the orientation detector 46, the display controller 43 inverts a color of the title bar 63, and also changes the display position of the window 61 in response to the movement of the line of sight of the operator Op. When the operator Op gazes at the title bar 63 again, the display controller 43 puts the color of the title bar 63 back to the original and fixes the display position of the window 61.

An ultrasonic image 66 is displayed from center to left side of the image display area 64. Although the 2D ultrasonic image (C-image described later) is displayed in the image display area 64 as an example here, the ultrasonic image 66 displayed in the image display area 64 is updated by a newly generated ultrasonic image of various types generated by the ultrasonic image generating section 42 in real time. When the ultrasonic image generating section 42 generates the 2D ultrasonic image like C-image, S-image, A-image or the like, the generated 2D ultrasonic image is displayed in the image display area 64. When the ultrasonic image generating section 42 generates the 3D ultrasonic image, the generated 3D image is displayed in the image display area 64. In addition, a scale showing a depth inside of the patient Pa's body is displayed on a left side of the ultrasonic image 66. On the right side of the ultrasonic image 66 is shown a variety of information 68 including date and time, setting condition of the ultrasonic diagnostic apparatus 11, frequency and power of the transmitted ultrasonic waves, cross section direction of the displayed 2D ultrasonic image with respect to the scanning area, and the like.

Figure 7C:
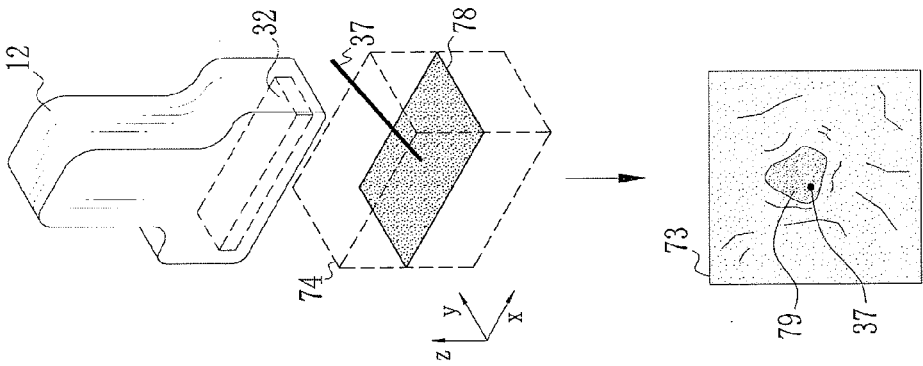
FIGS. 7A to 7C are explanatory views illustrating 2D ultrasonic images displayed by the ultrasonic diagnostic apparatus.
Figure 7B:
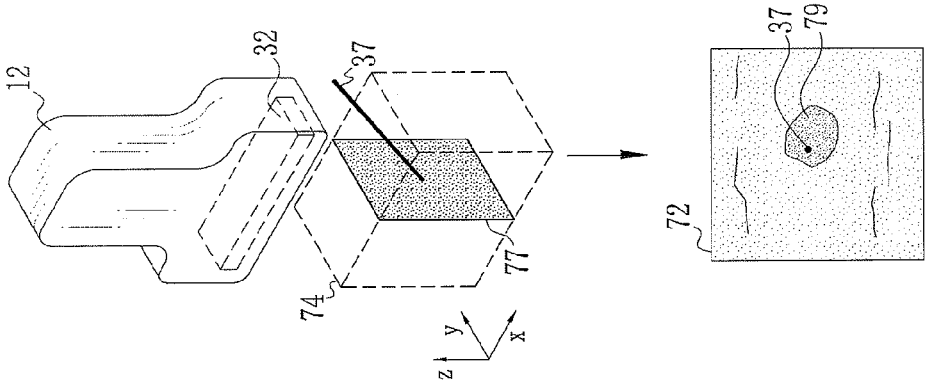
Figure 7A:
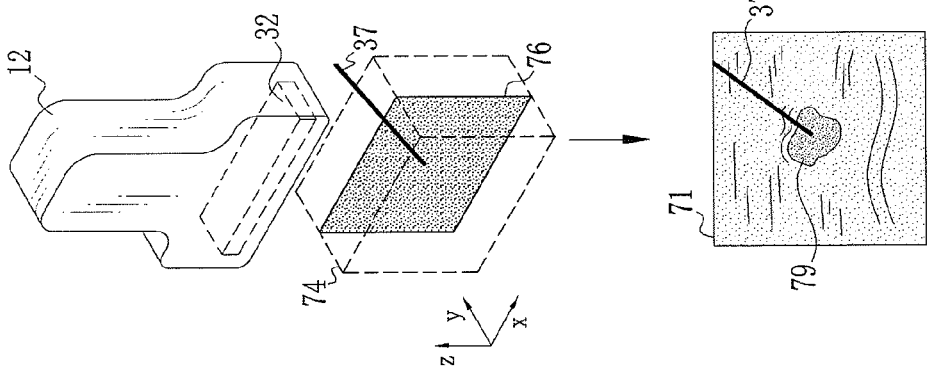

As shown in FIGS. 7A to 7C, to generate or display the 2D ultrasonic image in the ultrasonic diagnostic apparatus 11, one of three types of 2D ultrasonic images: C-image 71, S-image 72 and A-image 73, whose directions are preliminary determined while using the ultrasonic probe 12 as a reference, is selectively generated or displayed. In FIG. 7A, the C-image 71 is the 2D ultrasonic image along a coronal surface (C-surface) 76 perpendicular to a lateral or short direction (y-direction) of the ultrasonic transducer array 32 in the three-dimensional scanning area 74. In addition, the C-surface 76 passes through the center of the scanning area 74 in the y-direction. When the biopsy needle 37 is punctured using the biopsy needle adaptor 36, the biopsy needle 37 is punctured along the C-surface 76. Therefore, a shadow of the biopsy needle 37 appears as a line in the C-image 71. The C-image 71 corresponds to the ultrasonic image generated or displayed using the 2D ultrasonic probe.

In FIG. 7B, the S-image 72 is the 2D ultrasonic image along a sagittal surface (S-surface) 77 perpendicular to a longitudinal direction (x-direction) of the ultrasonic transducer array 32 in the three-dimensional scanning area 74. In addition, the S-surface 77 passes through the center of the scanning area 74 in the x-direction. When the biopsy needle 37 is punctured using the biopsy needle adaptor 36, a shadow of the biopsy needle 37 appears almost as a dot when the biopsy needle 37 reaches the S-surface 77. In FIG. 7C, the A-image 73 is the 2D ultrasonic image along an axial surface (A-surface) 78 parallel to the x and y-directions in the three-dimensional scanning area 74. In addition, the A-surface 78 passes through the center of the scanning area 74 in a depth direction (z-direction) of the patient Pa's body. When the biopsy needle 37 is punctured using the biopsy needle adaptor 36, a shadow of the biopsy needle 37 appears almost as a dot when the biopsy needle 37 reaches the A-surface 78.

Note that the terms of "coronal", "sagittal" and "axial" surfaces are generally determined with reference to a human body (patient Pa's body). However, these terms in this specification are used with reference to the ultrasonic probe 12.

When a tumor 79 is situated in almost center of the scanning area 74 as shown in FIGS. 7A to 7C, the tumor 79 is shown in the C-image 71, S-image 72 and A-image 73, respectively different in the cross section from one another. The operator Op appropriately switches the 2D ultrasonic image displayed on the HMD 13 from among these three types of 2D ultrasonic images 71 to 73 by the head tracking control using the HMD 13, and puncture the biopsy needle 37 while confirming the insertion path of the biopsy needle 37 and the insertion position with respect to the tumor 79.

Hereinafter, operations of the ultrasonic diagnostic apparatus 11 are explained. In order to perform diagnosis or to puncture the biopsy needle 37 while observing the ultrasonic image 66 using the ultrasonic diagnostic apparatus 11, the operator Op connects the ultrasonic probe 12 to the main body 14. At this time, the HMD 13 is disconnected from the main body 14 or not activated while being connected to the main body 13, or the head tracking setting is turned off. The main controller 51 then notifies the ultrasonic image generating section 20 that the ultrasonic probe 12 is connected and activated, and the HMD 13 is not activated or the head tracking setting is turned off. The ultrasonic image generating section 42 then generates the 3D ultrasonic image based on the 3D data obtained with the ultrasonic probe 12. The operator Op pushes the distal end portion 33 of the ultrasonic probe 12 against the observed site of the patient Pa's body, and figures out the position and number of the tumor within the range of the observed site while checking the 3D ultrasonic image three-dimensionally representing the observed site on the monitor 17 and the HMD 13. Then, the operator Op activates the HMD 13 and turns on the head tracking setting. According to the position and the like of the tumor figured out by checking the 3D ultrasonic image, the operator Op adjusts the position where the ultrasonic probe 12 is pressed against with, as well as his own orientation while checking the hands 62 so as to display the window 61 at the position not bothering the procedures. While maintaining this orientation, the operator Op sets his orientation to be the standard (hereinafter, referred to as the standard orientation) during the procedures. The orientation detector 46 sets the orientation signals input from the HMD 13 at the time when the standard orientation is set up as the standard for measuring the rotation direction and the rotation angle of the HMD 13.

Figure 8C:
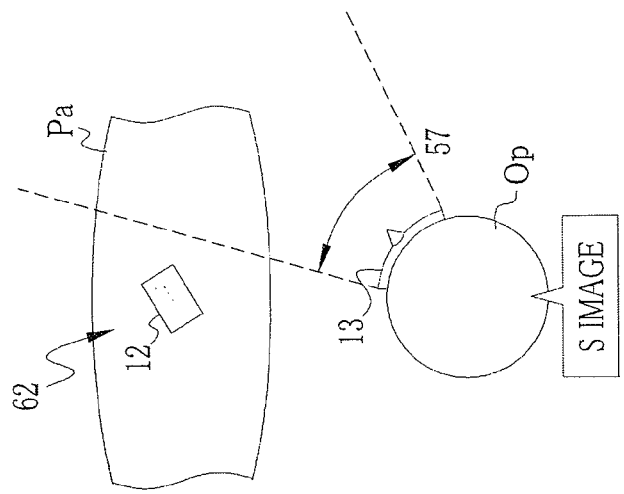
FIGS. 8A to 8C are explanatory views seen from above illustrating the states for switching the displayed 2D ultrasonic image.
Figure 8A:
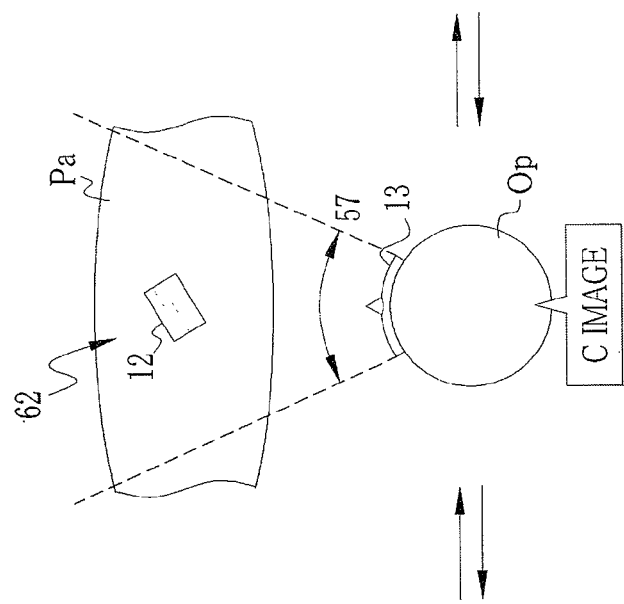
Figure 8B:
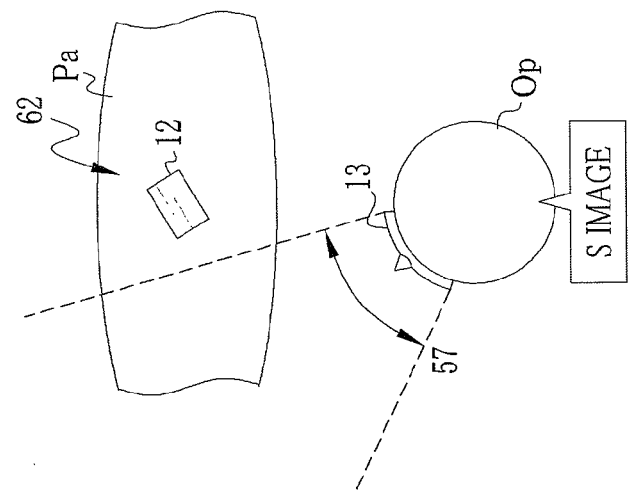

When the head tracking setting is turned on after the pre-observation like this, the ultrasonic image generating section 42 generates the 2D ultrasonic image based on the 3D data obtained with the ultrasonic probe 12 since the ultrasonic probe 12 and the HMD 13 are both activated. When the operator Op is in the standard orientation, as shown in FIG. 8A, the ultrasonic image generating section 42 generates the C-image 71. The operator Op can puncture the biopsy needle 37 to the patient Pa's body while observing the C-image 71. When the operator Op rotates his head to the left (FIG. 8B) or to the right (FIG. 8C), that is, in the horizontal direction, the orientation detector 46 measures the rotation direction and the rotation angle of the HMD 13 from the standard orientation. If the rotation direction of the HMD 13 is left or right and the rotation angle is ±60 degrees or more with respect to the standard orientation, the ultrasonic image generating section 42 switches the 2D ultrasonic image to be generated from the C-image 71 to the S-image 72. If the rotation direction of the HMD 13 is left or right and the rotation angle is less than 60 degrees, the ultrasonic image generating section 42 keeps generating the C-image 71. If the S-image 72 is needed to be observed for confirming the insertion path and the like of the biopsy needle 37, the operator Op rotates his head to left or right by ±60 degrees or more, and thereby observing the S-image 72.

If the operator Op rotates his head to left or right to move closer to the standard orientation after observing the S-image 72, the ultrasonic image generating section 42 generates the S-image 72 or the C-image 71 in response to the rotation angle. If the rotation angle from the standard orientation is ±40 degrees or more, the ultrasonic image generating section 42 generates the S-image 72 If the rotation angle from the standard orientation is less than ±40 degrees, the ultrasonic image generating section 42 switches the 2D ultrasonic image to be generated from the S-image 72 to the C-image 71. As described above, the HMD 13 needs to be rotated to left or right by ±60 degrees or more to switch from the C-image 71 to the S-image 72. However, even if the operator Op's head rotates excessively for 15 to 20 degrees from the angle where the display is supposed to be switched to the S-image 72 (±60 degrees), the S-image 72 is kept being displayed. In addition, the ultrasonic image generating section 42 switches the 2D ultrasonic image to be generated from the S-image 72 to the C-image 71 when the rotation angle from the standard orientation is less than ±40 degrees. For this configuration, in switching the 2D ultrasonic image displayed on the HMD 13 from the C-image 71 to the S-image 72, the 2D ultrasonic image is not unintentionally switched back and forth between the C-image 71 and the S-image 72 even if the operator Op's head shakes. That is, the 2D ultrasonic image which the operator Op requires can be stably displayed.

Figure 9A:
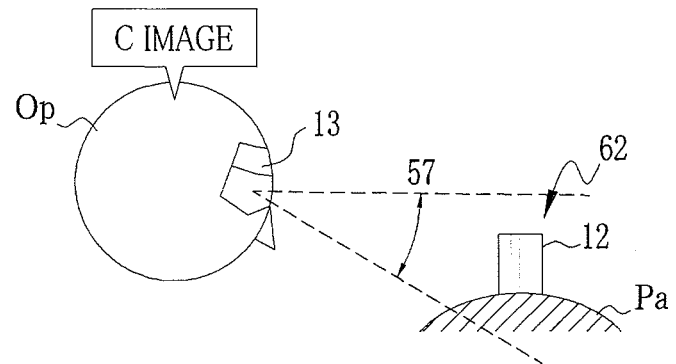
FIGS. 9A to 9C are explanatory views seen from side illustrating the states for switching the displayed 2D ultrasonic image.
Figure 9B:
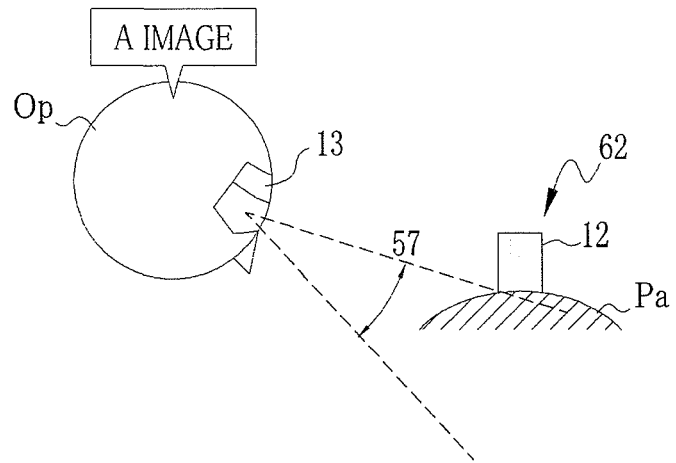
Figure 9C:
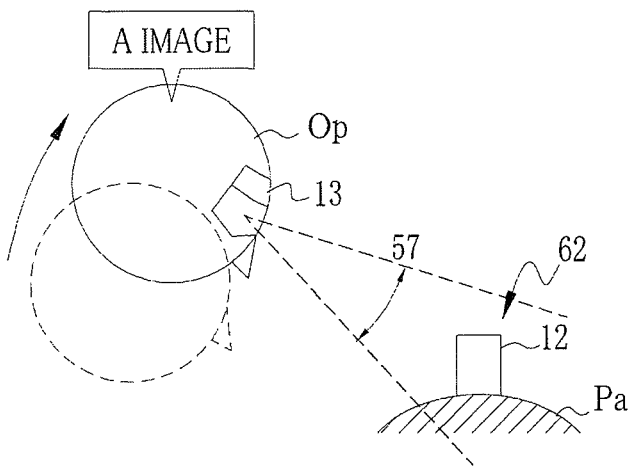

As described above, the 2D ultrasonic image displayed on the HMD 13 is switched between the C-image 71 and the S-image 72 when the operator Op rotates his head to right or left. When the operator Op rotates his head upward or downward, or the operator leans forward, the 2D ultrasonic image displayed on the HMD 13 is switched between the C-image 71 and the A-image 73 as shown in FIGS. 9A to 9C. In FIG. 9A, the C-image 71 is displayed on the HMD 13 when the operator Op observes the hands 62 in the standard orientation. When the operator Op rotates his head downward in the vertical direction by 60 degrees or more, the ultrasonic image generating section 42 switches the 2D ultrasonic image to be generated from the C-image 71 to the A-image 73. When the operator Op rotates his head upward in the vertical direction by 40 degrees or more after displaying the A-image 73, the ultrasonic image generating section 42 keeps generating the A-image 73, and when the operator Op rotates his head upward in the vertical direction by less than 40 degrees after displaying the A-image 73, the ultrasonic image generating section 42 switches the 2D ultrasonic image to be generated from the A-image 73 to the C-image 71. As described above, the HMD 13 needs to be rotated downward in the vertical direction by 60 degrees or more to switch from the C-image 71 to the A-image 73. However, even if the operator Op's head rotates excessively for 15 to 20 degrees from the angle where the display is supposed to be switched to the A-image 73 (±60 degrees), the A-image 73 is kept being displayed.

When the operator Op leans forward and rotates his head downward in the vertical direction while observing the hands 62, the ultrasonic image generating section 42 switches the 2D ultrasonic image to be generated from the C-image 71 to the A-image 73 if the rotation angle is 60 degrees or more. When the operator leans back to be close to the standard orientation, and rotates his head upward in the vertical direction while observing the hands 62, the ultrasonic image generating section 42 switches the 2D ultrasonic image to be generated from the A-image 73 to the C-image 71 if the rotation angle is less than 40 degrees. When the HMD 13 rotates or moves in a manner not explained in FIGS. 8A to 8C nor FIG. 9A to 9C, the ultrasonic image generating section keeps generating the 2D ultrasonic image which has been generated right before the rotation or the movement.

As described above, in the ultrasonic diagnostic apparatus 11, the 3D data is obtained using the 3D ultrasonic probe (ultrasonic probe 12), and the 2D ultrasonic image in the selected cross section from among the plurality of cross sections of the scanning area 74 for which the 3D data has been obtained is generated or displayed as necessary. Whether such 2D ultrasonic image needs to be generated or displayed is decided upon the connection status and the operation status of the HMD 13, and the setting of the head tracking. Owing to this, the 3D ultrasonic image can be used for the wide view observation (pre-observation) and the 2D ultrasonic image can be used for the procedure requiring precision. Therefore, the ultrasonic image appropriate for each procedure can be generated or displayed. In the ultrasonic diagnostic apparatus 11, the 2D image to be generated or displayed is switched in response to the rotation direction and the rotation angle of the HMD 13. Owing to this, the operator Op can easily observe the 2D ultrasonic image in a desired cross section of the scanning area 74 only by rotating the head on which the HMD 13 is mounted, even when both hands are occupied with the ultrasonic probe 12 and the treatment tools.

In the ultrasonic diagnostic apparatus 11, the 2D ultrasonic image to be displayed is selected from the three types of 2D ultrasonic images which are the C-image 71, the S-image 72 and the A-image 73. Owing to this, the operator Op does not need to fix his orientation as long as his orientation is within the certain range as compared to the case where the 2D ultrasonic image to be displayed is smoothly switched by following the line of sight of the operator. Therefore, the treatment tool such as the biopsy needle 37 is hardly lost even when the ultrasonic probe 12 or the orientation of the operator Op (HMD 13) shakes a little.

In the above embodiment, the C-image 71 is displayed when the operator Op is in the standard orientation, and the 2D ultrasonic image to be displayed is switched between the C-image 71 and the S-image 72 when the operator Op rotates his head to left or right (horizontally), and the 2D ultrasonic image to be displayed is switched between the C-image 71 and the A-image 73 when the operator Op rotates his head upward or downward (vertically). Hereinafter display examples in combinations of the horizontal rotation and the vertical rotation of the HMD 13 are explained.

Figure 10A:
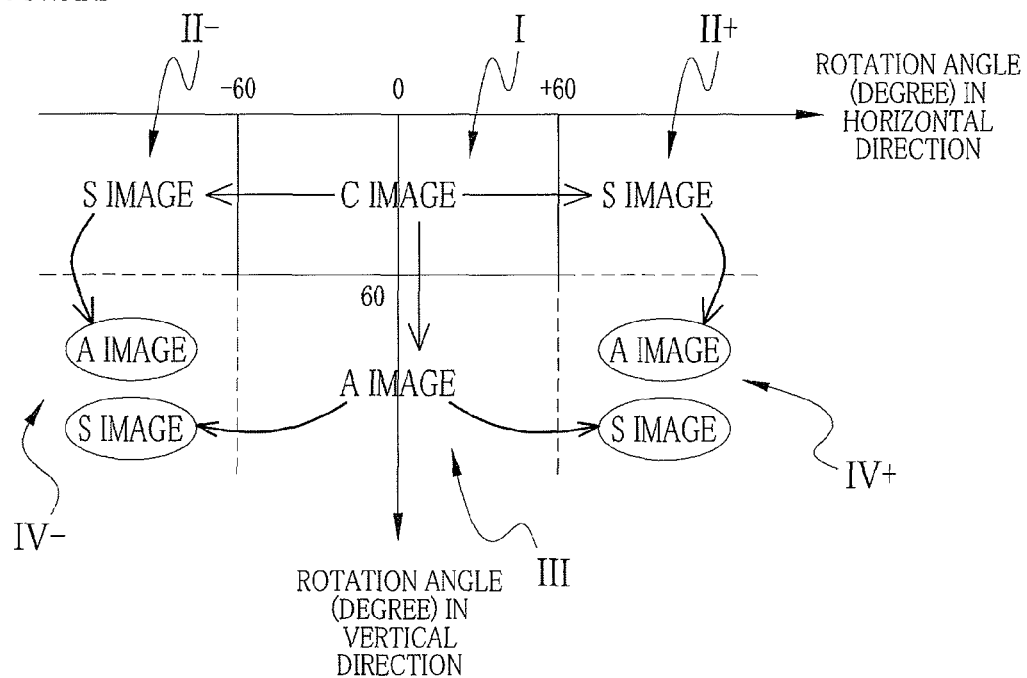
FIGS. 10A and 10B are explanatory views illustrating examples of the 2D ultrasonic images displayed in the case where the rotation in the horizontal direction and the rotation in the vertical direction are combined.

For example, in an outward rotation in which the HMD 13 is rotated in such a direction that the orientation of the HMD 13 becomes further from the standard orientation, as shown in FIG. 10A, the C-image 71 is displayed when the HMD 13 is in an area I in which the rotation angle in the horizontal direction (left or right) is less than ±60 degrees and the rotation angle in the vertical direction (upward or downward) is less than 60 degrees. In addition, when the HMD 13 is in an area II+ and an area II− in which the rotation angle in the horizontal direction is ±60 degrees or more and the rotation angle in the vertical direction is 60 degrees or more, the S-image 72 is displayed. Similarly, when the HMD 13 is in an area III in which the rotation angle in the horizontal direction is less than ±60 and the rotation angle in the vertical direction is 60 degrees or more, the A-image 73 is displayed. Accordingly, when the orientation of the HMD 13 is in the areas I, II± and III, the operations are the same as the above embodiment. When the HMD 13 is in an area IV± in which the rotation angle in the horizontal direction is ±60 degrees or more and the rotation angle in the vertical direction is ±60 degrees or more, the 2D ultrasonic image which has been displayed right before the rotation is kept being displayed. However, it is also possible that the A-image 73 is displayed when the orientation of the HMD 13 is changed from the area II± to the area IV±, and the S-image 72 is displayed when the orientation of the HMD 13 is changed from the area III to IV±. When the orientation of the HMD 13 is changed from the area II± to the area IV± for example, the operator Op is looking down or leaning forward to see the hands 62 from the state observing the S-image 72, and it may be preferable to display the A-image 73, as shown in FIG. 10A, as compared to keep displaying the S-image 72 as the above embodiment, so as to display the 2D ultrasonic image matches the operator's will. Such variation is applicable to the case where the orientation of the HMD 13 is changed from the area III to IV±.

Figure 10B:
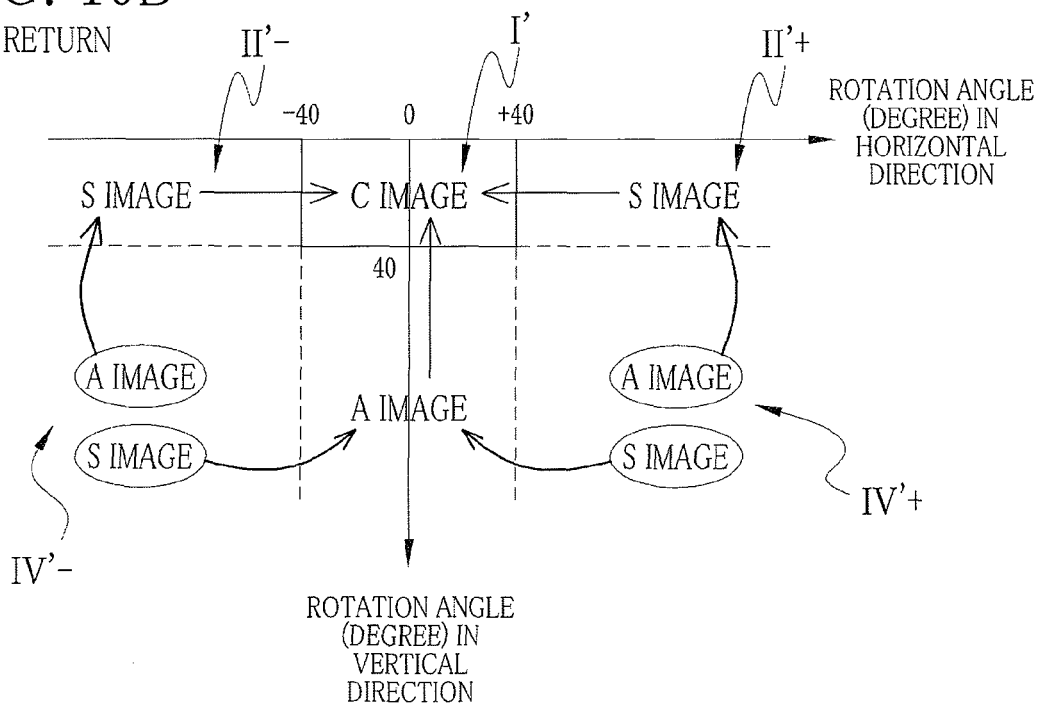

In a return rotation in which the HMD 13 is rotated in such a direction that the orientation of the HMD 13 becomes closer to the standard orientation, as shown in FIG. 10B, the image displayed in each of the areas I', II'±, III' and IV'± is the same as the above except that the rotation angle range in the horizontal direction is ±40 degrees and that in the vertical direction is 40 degrees. In addition, contrary to the above described, the 2D ultrasonic image specified in each area is displayed when the rotation of the HMD 13 is changed from the area IV'± to III' or II'±.

Figure 11A:
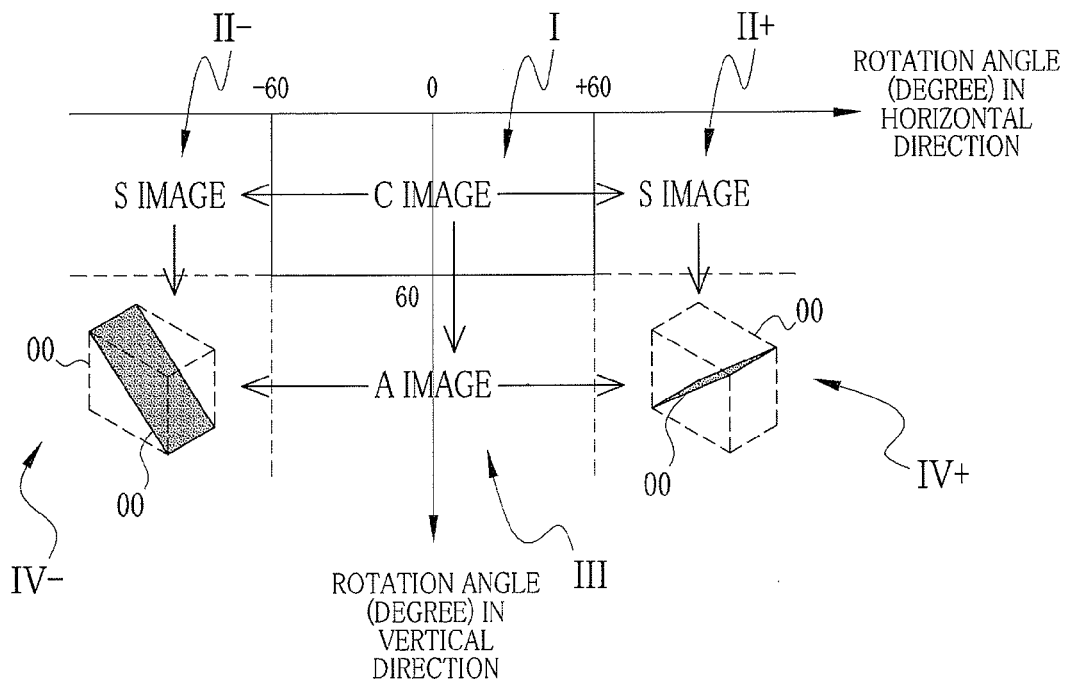
FIGS. 11A and 11B are explanatory views illustrating examples of the 2D ultrasonic images displayed in the case where the rotation in the horizontal direction and the rotation in the vertical direction are combined.
Figure 11B:
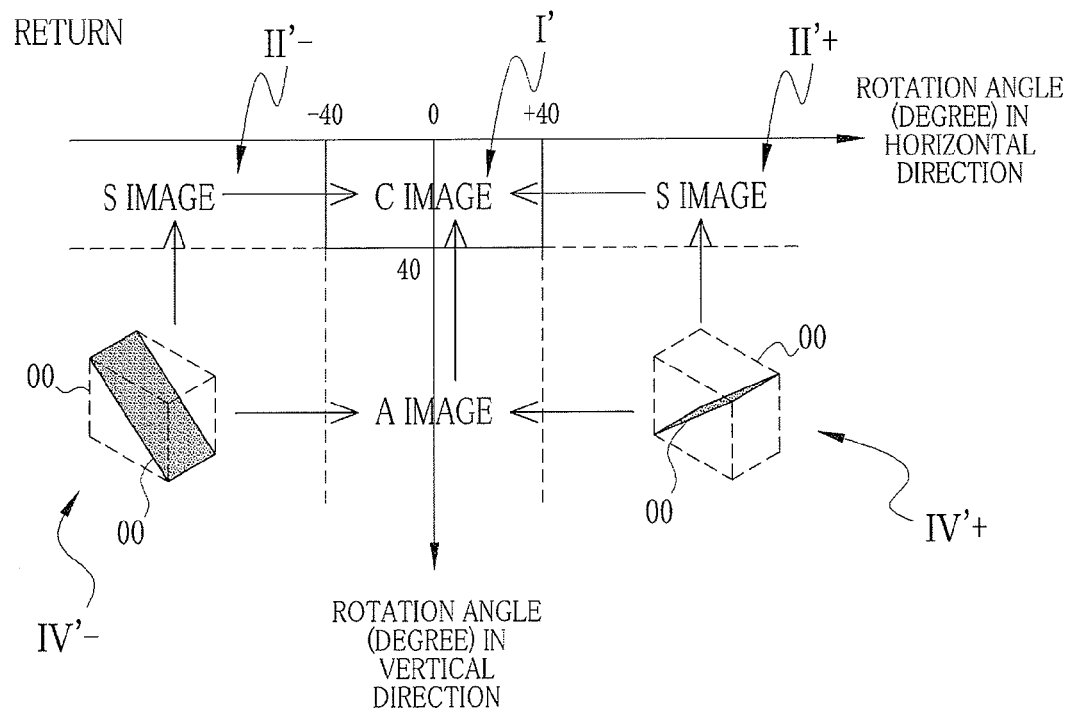

Here, the 2D ultrasonic images displayed in the IV± area in the outward rotation and in the IV'± area in the return rotation are the S-image 72 and the A-image 73, respectively. However, the 2D ultrasonic images displayed in the IV± area in the outward rotation and in the IV'± area in the return rotation are not necessarily selected from the C-image 72, the S-image 72 and the A-image 73. For example, when the orientation of the HMD 13 is in the IV-± area in the outward rotation and in the IV'± area in the return rotation, diagonal images 81*a* and 81*b* corresponding to the diagonal direction of the scanning area 74 may be generated in the ultrasonic image generating section 42, respectively, and displayed on the HMD 13, as shown in FIGS. 11A and 11B. In order to match the operator's will or desire as described above (FIGS. 10A to 10C), the diagonal images 81*a* and 81*b* may be combined after considering from which area the orientation of the HMD 13 is changed when orientation of the operator is in the IV± area in the outward rotation and in the IV'± area in the return rotation.

In the above embodiment, it is explained that the 2D ultrasonic image to be displayed is switched from the C-image 71 to the A-image 73 when the HMD 13 is rotated downward from the standard orientation as vertically downward direction is defined positive. It is also possible that the 2D ultrasonic image is switched between the C-image 71 and the A-image 73 under the angle range conditions symmetrical to the above embodiment when the HMD 13 is rotated upward from the standard orientation.

Figure 12:
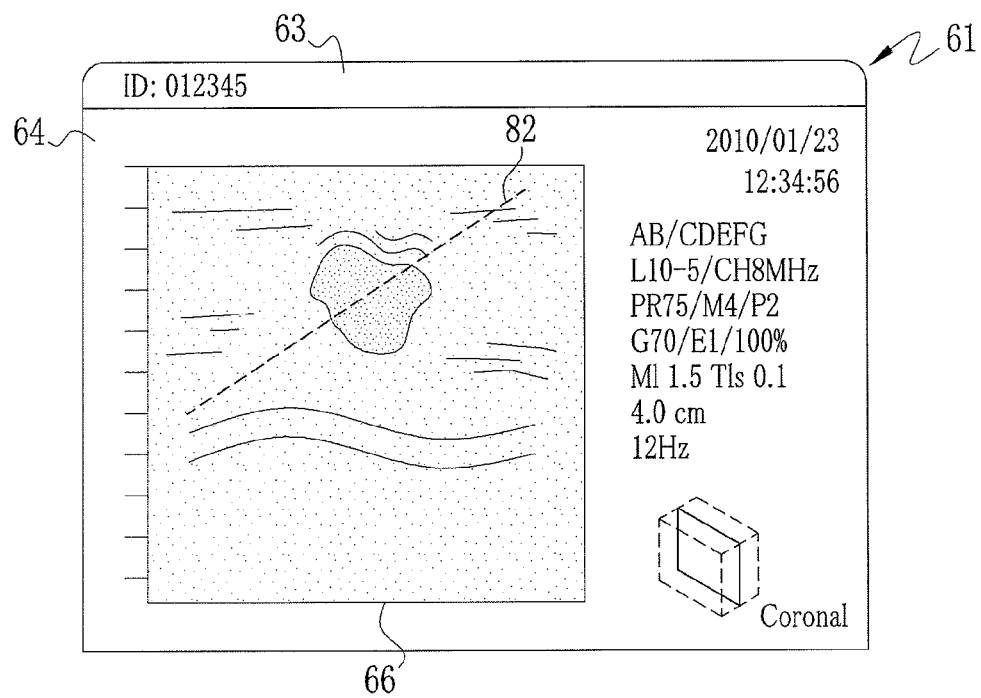
FIG. 12 is an explanatory view illustrating an example of superposing a biopsy guide on an image C.
Figure 13:
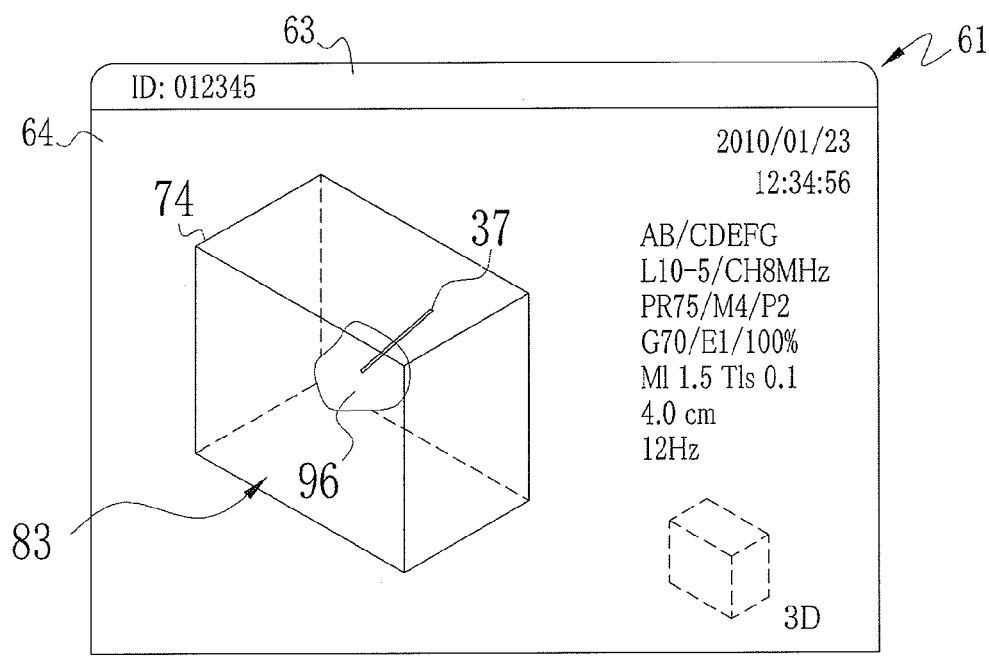
FIG. 13 is an explanatory view illustrating an example of displaying a 3D ultrasonic image.

In the above embodiment, the 2D ultrasonic image generated in the ultrasonic image generating section 42 is displayed as the ultrasonic image 66 on the HMD 13. The ultrasonic image 66 thus displayed on the HMD 13 preferably includes information necessary for the procedure interposed thereon. For example, when puncturing the biopsy needle 37 using the biopsy needle adaptor 36, the insertion position and the insertion angle of the biopsy needle 37 against the patient Pa's body are determined. Therefore, a biopsy guide 82 indicating the insertion direction of the biopsy needle 37 is preferably superposed onto the ultrasonic image 66 (C-image 71), as shown in FIG. 12. The biopsy guide 82 is preferably superposed at least onto the C-image 71.

In the above embodiment, although the 2D ultrasonic image is displayed on the HMD 13 during the procedure like puncturing the biopsy needle 37, a 3D ultrasonic image 83 may alternatively be displayed. Whether the 2D ultrasonic image is displayed or the 3D ultrasonic image 83 is displayed may appropriately be set or changed according to the type of the procedure or the operator Op's preference. When the 3D ultrasonic image 83 is displayed on the HMD 13, the direction of the displayed 3D ultrasonic image 83 is preferably changed according to the orientation of the operator Op with the HMD 13 mounted. If the direction of the displayed 3D ultrasonic image 83 needs to be adjusted, the head tracking function is preferably turned off.

In the above embodiment, although the ultrasonic transducers in the ultrasonic transducer array 32 are arranged in a rectangular form and the scanning area 47 is rectangular, the present invention is not limited to this, and other types of ultrasonic prove 12 is applicable as long as the ultrasonic transducer array 32 is arranged two-dimensionally. However, if the ultrasonic transducers are arranged in a square form on a flat plane, the C-surface 76 and the S-surface 77 within the scanning area 74 cannot be distinguished only from a directional property of the ultrasonic transducer array 32, and therefore the surfaces are preferably determined according to the shape of the ultrasonic probe 12 in advance. In the above embodiment, although the ultrasonic transducers of the ultrasonic transducer array 32 are arranged on a plane surface, the surface where the ultrasonic transducers are arranged may be curved like the 2D ultrasonic probe of convex type.

In the above embodiment, the C-image 71 is displayed when the HMD 13 is rotated horizontally by less than ±60 degrees and vertically by less than 60 degrees. When the HMD 13 is rotated horizontally by ±60 degrees or more from this state, the displayed image is switched to the S-image 72, while the displayed image is switched to the A-image 73 when the HMD 13 is vertically rotated by 60 degrees or more. Moreover, while the S-image 72 is being displayed, the image is switched to the C-image 71 if the horizontal rotation of the HMD 13 is made by less than ±40 degrees. While the A-image 73 is being displayed, the image is switched to the C-image 71 if the vertical rotation of the HMD 13 is made by less than 40 degrees. The ranges of degree for switching the display of the 2D ultrasonic image are not limited to the examples explained in the above embodiment, and may be arbitrary set according to the type of the procedure or the operator Op's preference. The ranges of degree for switching between the C-image 71 and the A-image 73 according to the rotation in the vertical direction are set in the same manner as the horizontal rotation described above. In the above embodiment, although the rotation angles for switching between the C-image 71 and the S-image 72 in the horizontal direction (±60 degrees in outward rotation, ±40 degrees in return rotation) and the rotation angles for switching between the C-image 71 and the A-image 73 in the vertical direction (60 degrees in outward rotation, 40 degrees in return rotation) are the same, these angles may be independently set at arbitrary angle according to the type of the procedure or the operator Op's preference.

In the above embodiment, the C-image 71 and the S-image 72 (A-image 73) are switched when the outward rotation of the HMD 13 is in the range of ±60 degrees (60 degrees) and the return rotation of the HMD 13 is in the range of ±40 degrees (40 degrees), and the angle ranges for switching the 2D ultrasonic image to be displayed are different from the outward rotation and the return rotation. However, the angle ranges for switching the 2D ultrasonic image are not limited to these examples, and the angle ranges may be same in the outward rotation and the return rotation (for example, 45 degrees in both rotations) when more sensitive and precise switching of the display is required. The accuracy in changing the display of the 2D ultrasonic image with respect to the rotation of the HMD 13 may arbitrary be set according to the operator Op's preference. When puncturing the needle, it is common that the C-image 71 is observed first, and the S-image 72 and the A-image 73 are used complementarily for checking the insertion path of the biopsy needle 37, and thus the 2D ultrasonic image needs not be changed often sensitively. In this case, the angle ranges for switching the display of the 2D ultrasonic image are varied between the outward rotation and the return rotation, and also the angle ranges for displaying the C-image 71 in the outward rotation (horizontally ±60 degrees and vertically 60 degrees) are made wider than that in the return rotation (horizontally ±40 degrees and vertically 40 degrees). Owing to this, the excessive switching of the display can be controlled. In the above embodiment, although the angle ranges for displaying the C-image 71 in the outward rotation is made wider than that in the return rotation, the angle rages may be inverted, that is, the angle ranges for displaying the C-image 71 in the outward direction is made smaller than that in the return rotation. In this case, the S-image 72 or the A-image 73 tends to be displayed longer, which facilitates the operator observe the image without rotating his head much Therefore, it may reduce the burden due to orientation regulation if the S-image 72 or the A-image 73 needs to be observed often during the procedure.

In the above embodiment, although the rotation direction and the rotation angle are both considered in changing the 2D ultrasonic image to be generated or displayed, the 2D ultrasonic image may be switched according to only one of the rotation direction and the rotation angle.

In the above embodiment, although three types of images, which are the C-image 71, the S-image 72 and the A-image 73, are generated or displayed as the 2D ultrasonic image, the present invention is not limited to this. The C-image 71 is the 2D ultrasonic image in the cross section passes the center of the scanning area 74. The 2D ultrasonic image crated by the ultrasonic image generating section 42 is not necessarily the cross section passes the center of the scanning area 74. That is, the C-image may be the cross section perpendicular to the y-direction in the scanning area 74, and generated at arbitrary position as long as it is perpendicular to the y-direction. In addition, the direction property of the scanning area 74 is not necessarily parallel to any of the directions of the C-image 71, the S-image 72 and the A-image 73. The 2D ultrasonic image may be generated in a cross section at arbitrary position in the scanning area 74 corresponding to the horizontal rotation or the vertical rotation of the HMD 13, like the diagonal images 81a and 81b. The cross section direction of the scanning area 74 for which the 2D ultrasonic image is generated may arbitrary be set according to the convenience in pressing the ultrasonic probe 12 to the observed site or the operator Op's preference.

In the above embodiment, the so called transmissive HMD 13 for projecting the window 61 in the actual view 57 is used. However, a nontransmissive HMD is also applicable in the ultrasonic diagnostic apparatus 11. When using the nontransmissive HMD, the window 61 showing the ultrasonic image 66 is superposed on an image capturing the view 57 of the operator Op, and displayed on the HMD.

Various changes and modifications are possible in the present invention and may be understood to be within the present invention.

What is claimed is:

1. An ultrasonic diagnostic apparatus comprising:
an ultrasonic probe in which ultrasonic transducers for transmitting ultrasonic waves and receiving echoes of said ultrasonic waves are two-dimensionally arranged, said ultrasonic probe configured to scan a three-dimensional area inside of a patient's body with said ultrasonic waves;
a tomographic image processor configured to generate a tomographic image of said three-dimensional area of the patient's body in a cross section, based on reception signals indicative of said echoes received by said ultrasonic transducers from inside of said patient's body;
a head mounted display configured to be mounted on a head of an operator, said head mounted display including an orientation detector configured to output signals corresponding to motion of the head of said operator and a projector configured to project at least said tomographic image in said operator's view;
a rotation measurement processor configured to measure rotation direction and rotation angle of the head of said operator on which said head mounted display is mounted with reference to a predetermined orientation of said head mounted display, based on the signals output from said orientation detector; and
a tomographic image switch section for switching said tomographic image projected by said projector, said cross section of said tomographic image is selected from a plurality of predetermined cross sections, according to said rotation direction and a range of said rotation angle measured by said rotation measurement section
and wherein in said tomographic switch image section, said rotation angle for switching said tomographic image is different between an outward rotation in which said head mounted display is rotated in a direction becoming further from said predetermined orientation and a return rotation in which said head mounted display is rotated in a direction becoming closer to said predetermined orientation.

2. The ultrasonic diagnostic apparatus according to claim 1, wherein said tomographic image processor obtains at least three predetermined cross sections, and said tomographic image switch selects said cross section according to a case where said head mounted display is in said predetermined orientation, a case where said head mounted display is horizontally rotated, and a case where said head mounted display is vertically rotated.

3. The ultrasonic diagnostic apparatus according to claim 1, wherein in said tomographic switch section, said rotation angle for switching said tomographic image is smaller in said return rotation than in said outward rotation.

4. The ultrasonic diagnostic apparatus according to claim 1, wherein in said tomographic switch section, said rotation angle for switching said tomographic image is variable.

5. The ultrasonic diagnostic apparatus according to claim 1, wherein said head mounted display displays a guide line indicating an insertion direction of a biopsy needle is superimposed upon said tomographic image based on at least one of said predetermined cross sections.

6. The ultrasonic diagnostic apparatus according to claim 1, wherein said tomographic image generating processor generates said tomographic image when said ultrasonic probe and said head mounted display are both activated.

7. The ultrasonic diagnostic apparatus according to claim 2, wherein said at least three predetermined cross sections include a first two-dimensional ultrasonic image along a coronal surface perpendicular to a short direction of an array of said ultrasonic transducers in a three-dimensional scanning area of said ultrasonic probe, said coronal surface passing through the center of said scanning area in said short direction, a second two-dimensional ultrasonic image along a sagittal surface perpendicular to a longitudinal direction of said array of said ultrasonic transducers in said three-dimensional scanning area, said sagittal surface passing through the center of said scanning area in said longitudinal direction, and a third two-dimensional ultrasonic image along an axial surface parallel to said short and longitudinal directions in said three-dimensional scanning area, said axial surface passing through the center of said scanning area in a depth direction of said patient's body.

8. The apparatus of claim 1, wherein the tomographic image switch section controls the projector to switch between display of the plurality of predetermined cross sections upon a detected range of rotation of the head mounted display exceeding 40 degrees from the predetermined orientation.

9. The apparatus of claim 7, wherein the tomographic switch section controls the projector to display the first two-dimensional ultrasonic image as a result of the case where said head mounted display is in said predetermined orientation, said first two-dimensional ultrasonic image being displayed until said rotation measurement processor determines that rotation of the head mounted display exceeds 60 degrees.

* * * * *